(12) United States Patent  
Yoo et al.

(10) Patent No.: US 7,879,337 B2
(45) Date of Patent: Feb. 1, 2011

(54) MUTANT PORCINE REPRODUCTIVE AND RESPIRATORY SYNDROME VIRUS

(75) Inventors: Dongwan Yoo, Guelph (CA); Changhee Lee, Guelph (CA); Jay Gregory Calvert, Otsego, MI (US)

(73) Assignee: Pfizer Inc., Madison, NJ (US)

( * ) Notice: Subject to any disclaimer, the term of this patent is extended or adjusted under 35 U.S.C. 154(b) by 209 days.

(21) Appl. No.: 11/718,828

(22) PCT Filed: Nov. 2, 2005

(86) PCT No.: PCT/IB2005/003366

§ 371 (c)(1),
(2), (4) Date: Jun. 11, 2008

(87) PCT Pub. No.: WO2006/051396

PCT Pub. Date: May 18, 2006

(65) Prior Publication Data

US 2009/0004221 A1   Jan. 1, 2009

Related U.S. Application Data

(60) Provisional application No. 60/626,767, filed on Nov. 11, 2004.

(51) Int. Cl.
*A61K 39/12* (2006.01)
*A61K 31/7088* (2006.01)
*C12N 7/00* (2006.01)
*C12N 7/02* (2006.01)
*C12N 7/04* (2006.01)
*C12N 5/10* (2006.01)
*C12N 15/40* (2006.01)

(52) U.S. Cl. .................. 424/204.1; 435/235.1; 435/236; 435/239; 435/325; 536/23.72; 514/44 R

(58) Field of Classification Search .................. None
See application file for complete search history.

(56) References Cited

U.S. PATENT DOCUMENTS 6,500,662 B1   12/2002 Calvert et al.
2002/0172690 A1   11/2002 Calvert et al.
2003/0157689 A1   8/2003 Calvert et al.

FOREIGN PATENT DOCUMENTS

| EP | 1 438 969 | 7/2004 |
|---|---|---|
| WO | 00/65032 | 11/2000 |
| WO | 02/095040 | 11/2002 |
| WO | 03/062407 | 7/2003 |

OTHER PUBLICATIONS

Kim et al (Journal of Clinical Microbiology 46:1758-1768, 2008).*
McKee et al (American Journal of Tropical Medicine and Hygiene 36:435-442, 1987).*
Lorroengsil et al (Southeast Asian Journal of Tropical Medicine and Public Health 39:387, 2008).*
Monath et al (Journal of Virology 76:1932-1943, 2002).*
Murphy et al (Journal of Clinical Investigation 110:21-27, 2002).*
Newman et al (Journal of Virology, 78:2017-2028, 2004).*
Parkman (Clinical Infectious Diseases, 28(Suppl 2):S140-6, 1998).*
Argnani et al (Gene Therapy, 12:S170-S177, 2005).*
PCT International Search Report, PCT/IB2005/003366, mailed Apr. 25, 2006.
Yoo, Database UniProt [Online] 2000, Database accession No. Q9PZ71.
Lee and Yoo, "Cysteine residues of the porcine reproductive and respiratory syndrome virus small envelope protein are non-essential for virus infectivity", Journal of General Virology, vol. 86, 2005, pp. 3091-3096.
Yoo et al., "Infectious cDNA clones of porcine reproductive and respiratory syndrome virus and their potential as vaccine vectors", Veterinary Immunology and Immunopathology, vol. 102, No. 3, 2004, pp. 143-154.
Wu et al., "A 10-kDa Structural Protein of Porcine Reproductive and Respiratory Syndrome Virus Encoded by ORF2b", Virology, vol. 287, 2001, pp. 183-191.
Snijder et al., "Identification of a Novel Structural Protein of Arteriviruses", Journal of Virology, vol. 73, No. 8, 1999, pp. 6335-6345.
Wootton and Yoo, "Homo-Oligomerization of the Porcine Reproductive and Respiratory Syndrome Virus Nucleocapsid Protein and the Role of Disulfide Linkages", Journal of Virology, vol. 77, No. 8, 2003, pp. 4546-4557.

* cited by examiner

*Primary Examiner*—Mary E Mosher
(74) *Attorney, Agent, or Firm*—Brandon Boss; E. Victor Donahue

(57) ABSTRACT

The present invention provides a genetically modified PRRS virus which has been modified such that the conserved cysteine in the E protein has been deleted or changed to a non-cysteine residue and polynucleotides that encode it. Vaccines comprising the genetically modified virus and polynucleotides are also provided.

17 Claims, 3 Drawing Sheets

Figure 3

```
 1MGSIQSLFDKIGQLFVDAFTEFLVSIVDIIIFLAILFGFTIAGWLVVFCIRLVCSAVFRARPAIHPEQLQKIL73    P129
 1MGSMQSLFDKIGQLFVDAFTEFLVSIVDIIIFLAILFGFTIAGWLVVFCIRLVCSAILRTRPAIHSEQLQKIL73    VR-2332
 1MG---SLWSKISQLFVDAFTEFLVSVVDIAIFLAILFGFTVAGWLLVFLLRVVCSALLRSRSAIHSPELSKVL70    Lelystad

US 7,879,337 B2

MUTANT PORCINE REPRODUCTIVE AND RESPIRATORY SYNDROME VIRUS

This application is a 371 application of PCT/2005/003366 filed Nov. 2, 2005, which claims the benefit of priority to U.S. provisional application Ser. No. 60/626,767 filed Nov. 11, 2004.

FIELD OF THE INVENTION

The present invention provides a genetically modified PRRS virus and polynucleotides that encode it. Vaccines comprising the genetically modified virus and polynucleotides are also provided.

BACKGROUND OF THE INVENTION

Porcine reproductive and respiratory syndrome (PRRS) is characterized by abortions, stillbirths, and other reproductive problems in sows and gilts, as well as respiratory disease in young pigs. The causative agent is the PRRS virus, a member of the family Arteriviridae and the order Nidovirales. Two distinct genotypes of the virus emerged nearly simultaneously in North America and in Europe in the late 1980's. PRRS virus is now endemic in nearly all swine producing countries, and is considered one of the most economically important diseases affecting the global pork industry.

Currently, commercial vaccines against PRRS include modified live and killed (inactivated) vaccines. Killed vaccines have been criticized for failing to induce robust immunity against heterologous strains of PRRS virus. Modified live vaccines are attenuated by serial passage in cell culture until virulence is lost. Modified live vaccines elicit broader protection than killed vaccines, but can suffer from a number of safety concerns including residual virulence, spread to non-vaccinated pigs, and genetic reversion to virulence. Because of antigenic changes that take place during the attenuation process, such vaccines can also lose some ability to protect against virulent field strains of PRRS virus. There is a pressing need therefore for new and improved modified live vaccines to protect against PRRS.

BRIEF DESCRIPTION OF THE DRAWINGS

FIG. 3. Alignment of E protein for North American and European isolates of PRRS virus (see SEQ ID NO:5 for E-protein of the North American P129 isolate, SEQ ID NO:31 for the North American VR-2332 isolate, and SEQ ID NO:32 for the European Lelystad isolate).

BRIEF DESCRIPTION OF THE SEQUENCES

Figure 1:
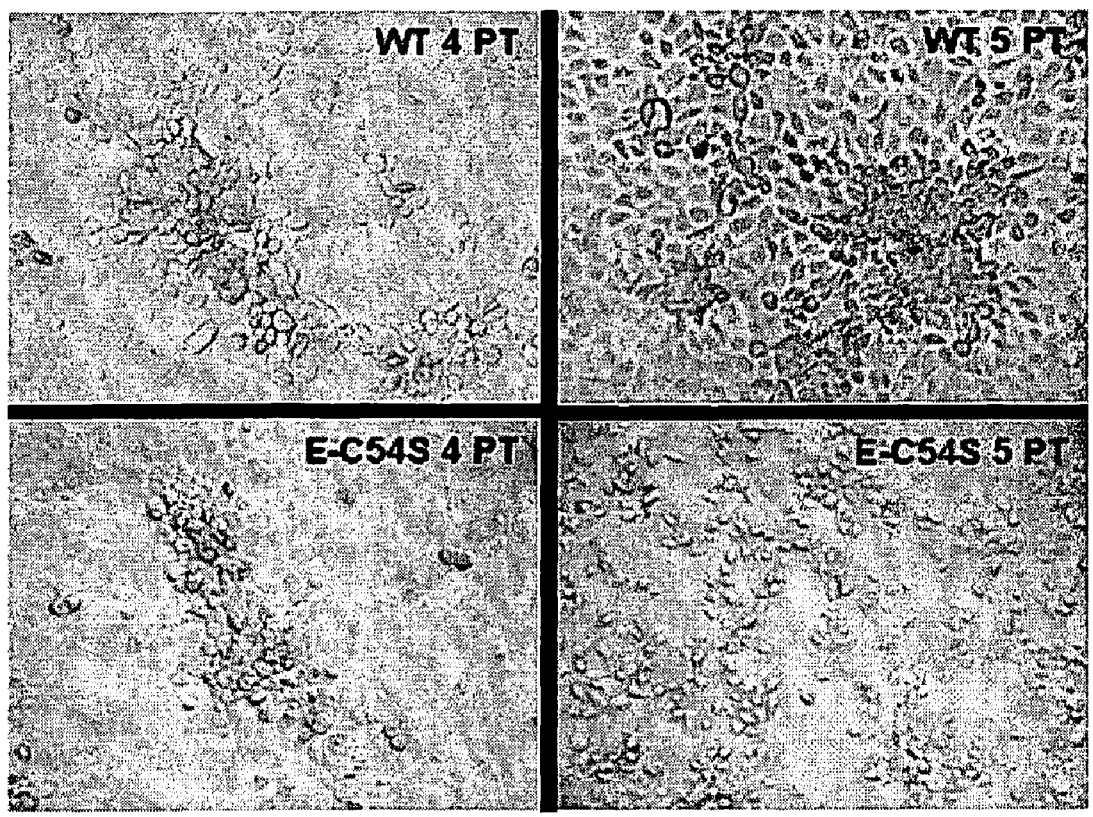
FIG. 1. Cytopathic Effect (CPE) in MARC-145 cells at 4 days (left) and 5 days (right) post-transfection using parental cDNA clone pCMV-S-P129 (top) or mutant cDNA clone pCMV-S-P129-E-C54S (bottom).

SEQ ID NO: 1 Shuttle Plasmid PTB-Shuttle-PRRSV-3997 Primer Shuttle Forward
SEQ ID NO: 2 Shuttle Plasmid PTB-Shuttle-PRRSV-3997 Primer Shuttle Reverse
SEQ ID NO: 3 Mutagenic Primers2b-C54s-Forward
SEQ ID NO: 4 Mutagenic Primers2b-C54s-Forward
SEQ ID NO: 5 E Protein of PRRSV P129
SEQ ID NO: 6 cDNA for E Protein PRRSV 129
SEQ ID NO: 7 Mutated ORF2b
SEQ ID NO: 8 Peptide for Mutated ORF2b
SEQ ID NO: 9, 11, 15, 19, 23, 27 Various C54s Mutations—Nucleoltide sequences
SEQ ID NO: 10, 12, 16, 20, 24, 28 Various C54s Mutations—Pepetides
SEQ ID NO: 13, 14, 17, 18, 21, 22, 25, 26, 29, 30 Forward (F) and Reverse (R) Mutagenic Primers for C54s Mutations

SUMMARY OF THE INVENTION

The invention provides a genetically modified PRRS virus which has been modified such that the conserved cysteine in the E protein has been deleted or changed to a non-cysteine residue.

The invention further provides a genetically modified PRRS virus which has been modified such that the conserved cysteine in the E protein has been deleted or changed to a non-cysteine residue with the proviso that the non-cysteine residue is not tyrosine.

The subject invention further provides an infectious RNA molecule encoding the genetically modified virus recited above The subject invention further provides an isolated polynucleotide molecule comprising a DNA sequence encoding an infectious RNA molecule recited above.

The invention also provides a biologically pure culture (i.e substantially free of other viruses) of the viruses recited.

The subject invention further provides a viral vector comprising a DNA sequence encoding an infectious RNA molecule encoding a genetically modified PRRS virus as recited above.

The subject invention further provides a transfected host cell comprising any of the forgoing viruses, infectious RNA molecules, isolated polynucleotides or viral vectors recited above.

The subject invention further provides a vaccine for protecting a porcine animal from infection by a PRRS virus, which vaccine comprises a genetically modified PRRS virus as recited above; an infectious RNA molecule as recited above encoding the genetically modified PRRS virus; an isolated polynucleotide molecule recited above, (optionally in the form of a plasmid), encoding the genetically modified PRRS virus; or the above-recited viral vector encoding the genetically modified PRRS virus; in an amount effective to produce immunoprotection against infection by a PRRS virus; and a carrier acceptable for veterinary use.

The subject invention further provides a method for protecting a porcine animal from infection by a PRRS virus, which comprises vaccinating the animal with an amount of the above-recited vaccine that is effective to produce immunoprotection against infection by a PRRS virus.

The invention provides a method for making a genetically modified PRRS virus, which method comprises mutating the DNA sequence encoding an infectious RNA molecule which encodes the PRRS virus as described above, and expressing the genetically modified PRRS virus using a suitable expression system.

A PRRS virus, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

Other features of the invention will be evident upon review.

DETAILED DESCRIPTION OF THE INVENTION

We disclose herein a method of attenuating a virulent PRRS virus by mutating or deleting a specific cysteine residue found in the E (or 2b) protein of the virus, an immunogenic composition comprising said attenuated virus, and a method of protecting swine from PRRS by vaccination with said immunogenic compositions. PRRS viruses that have been attenuated by this method should retain the antigenic characteristics of the virulent field strain and therefore afford more potent protection than vaccines based on cell culture attenuated viruses.

Arteriviruses encode a small hydrophobic structural protein provisionally named the envelope (E) protein. (Snijder, E. J., et al. (1999). Identification of a novel structural protein of arteriviruses. Journal of Virology 73(8), 6335-6345).

The function of the E protein is not known, but it is conserved in all arteriviruses. Knockout mutations in equine arteritis virus have shown that the E protein is essential for virus replication in cell culture. Unlike the other structural proteins of the PRRS virus, which are each encoded by a corresponding unique subgenomic RNA, the E protein and the GP2 protein share a single subgenomic RNA. ORF2b (which encodes E) is completely contained within the larger ORF2a (which encodes GP2) and utilizes a different reading frame. Although the ATG initiation codon of ORF2b is located downstream of ORF2a initiation codon, it is in a more favorable context for translation initiation and is probably the primary-product produced from this subgenomic RNA. (Wu, W. H., et al. (2001). A 10-kDa structural protein of porcine reproductive and respiratory syndrome virus encoded by ORF2b. Virology 287(1), 183-191)

North American genotype PRRS viruses generally contain two cysteine residues within the amino acid sequence of their E proteins, at positions 49 and 54. Using an infectious cDNA clone of North American PRRS isolate P129, C49 and C54 were individually mutated to serine. The resulting C49S mutation was viable. Similarly, the C54S mutation was also viable and produced high yields of progeny virus from the infectious clone. The P129-E-C49S and P129-E-C54S virus was readily passaged and titrated on MARC cells. However, the P129-E-C54S virus displayed altered plaque morphology (small, clear plaques) and accelerated cytopathic effect (CPE). This mutation should lead to attenuation in the pig.

European genotype PRRS viruses contain a single cysteine residue at position 51, which corresponds precisely with C54 in North American PRRS virus when the E protein sequences are aligned. We expect that elimination of C51 in European PRRSV E protein (by deletion or substitution) will have an altered phenotype similar to P129-E-C54S in cell culture and will be attenuated in pigs. (As noted below we designate the cysteine residue present in both North American PRRS and European PRRS E proteins as a "conserved cysteine") Viral mutations of this type are valuable, either alone or in combination with other attenuating mutations, for designing novel PRRS vaccines.

DEFINITIONS

CPE is cytopathic effect.

The term PRRSV "E protein" or "ORF2b protein" as used herein is defined as a polypeptide that is encoded by ORF2b of both the European and American isolates of PRRS virus. Unlike the other structural proteins of the PRRS virus, which are each encoded by a corresponding unique subgenomic RNA, the E protein and the GP2 protein share a single subgenomic RNA. ORF2b (which encodes E) is completely contained within the larger ORF2a (which encodes GP2) and utilizes a different reading frame. Although the ATG initiation codon of ORF2b is located downstream of ORF2a initiation codon, it is in a more favorable context for translation initiation and is probably the primary product produced from this subgenomic RNA (Wu et al., 2001).

The term "European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus".

The term "genetically modified", as used herein and unless otherwise indicated, means genetically mutated by human intervention.

The term "host cell capable of supporting PRRS virus replication" means a cell line that is capable of generating infectious PRRS when either infected or transfected with a virus or polynucleotide of the invention. Such cells include porcine alveolar macrophage cells and derivatives of porcine alveolar macrophage cells, MA-104 cells and derivatives of MA-104 cells, MARC-145 cells and derivatives of MARC-145 cells. Especially preferred for the demonstrating the small plaque phenotype of the invention are MARC-145 cells. The term "host cell capable of supporting PRRS virus replication" may also include cells within a live pig.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

The term "mutated" means the replacement of an amino acid for another or the replacement of the coding nucleotide by another (e.g. C for a T), i.e., a so-called "substitution", preferably in a way that the encoded amino acid is changed, or any other mutation such as "deletion" or "insertion". The mutation is always carried out in the coding nucleotide sequence.

The term "North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate MN-1b (Kwang, J. et al., 1994, J. Vet. Diagn. Invest. 6:293-296); the Quebec IAF-exp91 strain of PRRS (Mardassi, H. et al., 1995, Arch. Virol. 140:1405-1418); and North American PRRS virus isolate VR 2385 (Meng, X.-J et al., 1994, J. Gen. Virol. 75:1795-1801). Genetic characteristics refer to genomic nucleotide sequence similarity and amino acid sequence similarity shared by North American PRRS virus strains.

The term "open reading frame", or "ORF", as used herein, means the minimal nucleotide sequence required to encode a particular PRRS virus protein without an intervening stop codon.

The terms "porcine" and "swine" are used interchangeably herein and refer to any animal that is a member of the family Suidae such as, for example, a pig. The term "PRRS virus", or "PRRSV", as used herein, unless otherwise indicated, means any strain of either the North American or European PRRS viruses.

As used herein, the term "PRRS" encompasses disease symptoms in swine caused by a PRRS virus infection. Examples of such symptoms include, but are not limited to, abortion in pregnant females, and slow growth, respiratory difficulties, loss of appetite, and mortality in young pigs. As used herein, a PRRS virus that is "unable to produce PRRS" refers to a virus that can infect a pig, but which, either does not produce any disease symptoms normally associated with a PRRS infection in the pig, or produces such symptoms, but to a lesser degree, or produces a fewer number of such symptoms, or both, as compared to a wild type virulent infection.

The term "transfected host cell" means practically any host cell such as is described in U.S. Pat. No. 5,600,662, incorporated herein by reference, when transfected with PRRS virus RNA can produce a first round of PRRS virions. If further productive infection is desired a "host cell capable of supporting PRRS virus replication" as defined below would be used.

Polynucleotide molecules can be genetically mutated using recombinant techniques known to those of ordinary skill in the art, including by site-directed mutagenesis, or by random mutagenesis such as by exposure to chemical mutagens or to radiation, as known in the art. Said mutations may be carried out by standard methods known in the art, e.g. site directed mutagenesis (see e.g. Sambrook et al. (1989) Molecular Cloning: A Laboratory Manual, 2(nd) ed., Cold Spring Harbor Laboratory Press, Cold Spring Harbor, N.Y.) of an infectious copy as described (e.g. Meulenberg et al., Adv. Exp. Med. Biol, 1998, 440:199-206).

Accordingly, the subject invention further provides a method for making a genetically modified North American PRRS virus, which method comprises mutating the DNA sequence encoding an infectious RNA molecule which encodes the PRRS virus as described above, and expressing the genetically modified PRRS virus using a suitable expression system. A genetically modified PRRS virus can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro, as is described in further detail below.

Examples of specific isotypes of E protein which are currently known are the 73 amino acid polypeptide of American PRRS as predicted by the sequence reported in Genbank Accession number U87392 (also known as VR2332) at genome positions 12,078-12,299, and as predicted by the sequence in Genbank Accession number AF494042 (also known as P129) and reported as protein AAM18560.1, and the 70 residue European PRRS E protein as predicted by Genbank Accession number M96262 (also known as the Lelystad isolate) at genome positions 11,801-12,013.

The North American PRRSV E protein sequences are highly conserved and the reported sequences have about 93% identity with each other. The North American and European PRRSV E proteins are about 83% identical and share (among many other residues) a conserved cysteine at residue 54 of the VR2332 and P129 E protein isolates and residue 51 of the Lelystad isolate E protein. FIG. 3 allows visualization of the cysteine which we have designated as the "conserved cysteine", i.e. the cysteine conserved between European and American PRRS isolates. The numbering of amino acids referenced above is according to the database entries mentioned. In all other PRRS isolates, which might be numbered differently, identification of the proper cysteine is readily achieved by identifying preserved characteristic amino acids in a PRRS strain of interest and aligning it with a reference strain. It is an object of the present invention to modify a PRRS virus or its encoding nucleic acids such that the conservative cysteine is eliminated either by substitution, deletion or insertion such that it results in a small plaque phenotype.

Deletions or substitutions that eliminate the conserved cysteine are introduced by modification of polynucleotides encoding viruses of the invention. In a preferred embodiment a deletion or insertion comprises 1, 2, 3, 4 5, 6, 7, 8, 9, or 10 amino acids that result in the elimination of the conserved cysteine and in which said deletion or substitution results in small plaque phenotype in the resultant virus. A preferred embodiment would be a deletion or insertion of 5 or less amino acids.

Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (from WO 97/09433, page 10, published Mar. 13, 1997 (PCT/GB96/02197, filed Sep. 6, 1996), immediately below.

TABLE A

CONSERVATIVE SUBSTITUTIONS I

| SIDE CHAIN CHARACTERISTIC | AMINO ACID |
| --- | --- |
| Aliphatic | |
| Non-polar | G A P |
|  | I L V |
| Polar-uncharged | C S T M |
|  | N Q |
| Polar-charged | D E |
|  | K R |
| Aromatic | H F W Y |
| Other | N Q D E |

Alternatively, conservative amino acids can be grouped as described in Lehninger, [Biochemistry, Second Edition; Worth Publishers, Inc. NY:N.Y. (1975), pp. 71-77], as set out in Table B, immediately below.

TABLE B

CONSERVATIVE SUBSTITUTIONS II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table C, immediately below.

TABLE C

CONSERVATIVE SUBSTITUTIONS III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Preparation of Genetically Modified PRRS Virus

Recombinant DNA technology comprises extremely varied and powerful molecular biology techniques aimed at modifying nucleic acids at the DNA level and makes it possible to analyze and modify genomes at the molecular level. In this respect viruses such as the PRRS virus, because of the small-size of its genome, is particularly amenable to such manipulations. However, recombinant DNA technology is not immediately applicable to nonretroviral RNA viruses because these viruses do not encompass a DNA intermediate step in their replication. For such viruses infectious cDNA clones have to be developed before recombinant DNA technology can be applied to their genome to generate modified virus. Infectious clones can be derived through the construction of full-length (genomic length) cDNA (here used in the broad sense of a DNA copy of RNA and not only in the strict sense of a DNA copy of mRNA) of the virus under study after which an infectious transcript is synthesized in vivo in cells transfected with the full-length cDNA. Infectious transcripts can also be obtained by in vitro transcription from full-length or ligated partial-length cDNA fragments that comprise the full viral genome. In all cases, the transcribed RNA carries all the modifications that have been introduced to the cDNA and can be used to further passage the thus modified virus.

The preparation of an infectious clone of a European PRRS virus isolate, Lelystad virus, is described in U.S. Pat. No. 6,268,199 Meulenberg et al., Jul. 31, 2001, which is hereby fully incorporated by reference. The preparation of an infectious cDNA clone of a North American PRRS virus isolate designated P129 is described in U.S. Pat. No. 6,500,662 Calvert et al., Dec. 31, 2002, which is hereby incorporated fully by reference. The sequence of P129 cDNA is disclosed in Genbank Accession Number AF494042 and in U.S. Pat. No. 6,500,662 Calvert et al., Dec. 31, 2002. Our work below makes use of such an infectious clone which in the context of a plasmid is expressed by the CMV immediate early promoter and has been designated pCMV-S-P129 and is also disclosed within U.S. Pat. No. 6,500,662, Calvert et al., Dec. 31, 2002. As described in U.S. Pat. No. 6,500,662 Calvert et al., Dec. 31, 2002, other plasmids and promoters are also suitable.

It is apparent that given the complete sequence of any open reading frame of interest and the location of an amino acid residue of interest one of ordinary skill need merely consult a codon table to design changes at the particular position desired.

TABLE D

Coding Sequence from E protein of P129 isolate

```
  M   G   S   I   Q   S   L   F   D   K   I   G
ATG GGG TCT ATA CAA AGC CTC TTC GAC AAA ATT GGC

Q   L   F   V   D   A   F   T   E   F   L   V
CAG CTT TTT GTG GAT GCT TTC ACG GAA TTT TTG GTG

S   I   V   D   I   I   I   F   L   A   I   L
TCC ATT GTT GAT ATC ATC ATA TTT TTG GCC ATT TTG

F   G   F   T   I   A   G   W   L   V   V   F
TTT GGC TTC ACC ATC GCC GGT TGG CTG GTG GTC TTT

C   I   R   L   V   C   S   A   V   F   R   A
TGC ATC AGA TTG GTT TGC TCC GCG GTA TTC CGT GCG

R   P   A   I   H   P   E   Q   L   Q   K   I
CGC CCT GCC ATT CAC CCT GAG CAA TTA CAG AAG ATC

L   *
CTA TGA
```

A table of amino acids and their representative abbreviations, symbols and codons is set forth below in the following Table E.

TABLE E

| Amino | Abbrev. | Symbol | Codon(s) | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |

TABLE E-continued

| Amino | Abbrev. | Symbol | Codon(s) | | | | | |
|---|---|---|---|---|---|---|---|---|
| Methionine | Met | M | AUG | | | | | |
| Asparagine | Asn | N | AAC | AAU | | | | |
| Proline | Pro | P | CCA | CCC | CCG | CCU | | |
| Glutanune | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Theonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

As is well known in the art, codons constitute triplet sequences of nucleotides in mRNA and their corresponding cDNA molecules. Codons are characterized by the base uracil (U) when present in a mRNA molecule but are characterized by base thymidine (T) when present in DNA. A simple change in a codon for the same amino acid residue within a polynucleotide will not change the sequence or structure of the encoded polypeptide. It is apparent that when a phrase stating that a particular 3 nucleotide sequence "encode(s)" any particular amino acid, the ordinarily skilled artisan would recognize that the table above provides a means of identifying the particular nucleotides at issue. By way of example, if a particular three-nucleotide sequence encodes cysteine the table above discloses that the two possible triplet sequences are UGC (TGC if in DNA) and UGU (TGT if in DNA). Serine is encoded by AGC, AGU (AGT in DNA), UCA (TCA in DNA) and UCC (TCC in DNA), UCG (TCG in DNA) and UCU (TCT in DNA). To change a cysteine to serine residue in an encoded protein one might replace a TGC or TGT triplet with any of AGC, AGT, TCA, TCC, TCG or TCT in the encoding nucleic acid.

The construction of just such a mutant protein E polynucleotide sequence is demonstrated in the following by way of illustrative example.

Example 1

Construction of Shuttle Plasmid PTB-Shuttle-PRRSV-3997

A shuttle plasmid was constructed in order to facilitate the introduction of specific modifications to a full-length PRRS virus genomic cDNA clone. A 3,997 bp fragment, representing the extreme 3' end of the viral genome (nucleotide positions 11,504 to 15,416, including a 21 residue polyadenosine tail) and 84 bp of downstream vector sequences, was PCR-amplified. The PCR reaction included 5 ng of pCMV-S-P129 plasmid DNA (U.S. Pat. No. 6,500,662 B1), 300 ng of forward primer P-shuttle-Fwd SEQ ID NO: 1 (5'-ACTCAGTCTAAGTGCTGGAAAGTTATG-3': positions 11,504 to 11,530), 300 ng of reverse primer P-shuttle-Rev primers SEQ ID NO: 2 (5'-ATCTTATCATGTCTGGATCCCCGCGGC-3': positions 15,500 to 15,475), 1 mM each of dNTPs, 1×PCR buffer [10 mM KCl, 10 mM (NH$_4$)$_2$SO$_4$, 20 mM Tris-HCl (pH 8.8), 2 mM MgSO$_4$, 0.1% Triton X-100], and 2.5 U of Pfu DNA polymerase (Stratagene) using the GeneAmp PCR system 2400 (Perkin Elmer). The reaction was heated up for 5 min at 95° C. and subjected to 35 cycles of amplification under the following conditions; denaturation at 95° C. for 30 sec, primer annealing at 55° C. for 1 min, and extension at 72° C. for 3 min. The PCR product was cloned into the pTrueBlue vector using the TrueBlue MicroCartridge™ PCR Cloning Kit XL (Genomics One; Buffalo, N.Y.) to create pTB-shuttle-PRRSV-3997.

Example 2

Substitution of Cysteine Residue 54 In Protein E (Or 2B) To Generate P129-E-C54S Virus The E protein of PRRSV P129, which is encoded by ORF 2b, contains two cysteine residues at amino acid positions 49 and 54, see SEQ ID NO: 5 MGSIQSLFDKIGQLFVDAFT EFLVSIVDIIIFLAILFGFTIAGWLVVF CIRLVCSAVFRARPAIHPEQLQKIL. The cDNA for SEQ ID NO: 5 is SEQ ID NO:6 ATGGGGTCTATACAAAGC-CTCTTCGACAAAATTGGCC AGCTTTTTGTGGAT-GCTTTCACGGAATTTTTGGTGTCCAT-TGTTGATATCATCATATTT TTGGCCATTTTGTTTGGCTTCAC-CATCGCCGGTTGGCTGGTGGTCTTTTGCATCAGAT TGGTTTGCTCCGCGGTATTCCGT-GCGCGCCCTGCCATTCACCCTGAGCAATTACAGA AGATCCTATGA The cysteine residue at position 54 (nucleotide positions 12,221-12,223 in the P129 genome) was replaced with serine using PCR-based site-directed mutagenesis. Shuttle plasmid pTB-shuttle-PRRSV-3997 was used as template, with mutagenic primers 2b-C54S-Fwd SEQ ID NO: 3 (5'-GCAT-CAGATTGGTT<u>AGC</u>TCCGCGGTATTCCG-3': nucleotide positions 12,207 to 12,238) and 2b-C54S-Rev SEQ ID NO: 4 (5'-CGGAATACCGCGGA<u>GCT</u>AACCAATCTGATGC-3': nucleotide positions 12,207 to 12,238). The mutated codon is underlined. PCR amplifications were carried out using 5 ng of pTB-shuttle-PRRSV-3997 plasmid DNA, 300 ng each of the forward and reverse primers; 1 mM concentrations each of dCTP, dGTP, DATP, and dTTP, 1×PCR buffer [10 mM KCl, 10 mM (NH$_4$)$_2$SO$_4$, 20 mM Tris-HCl (pH 8.8), 2 mM MgSO$_4$, 0.1% Triton X-100]; and 2.5 U of Pfu DNA polymerase (Stratagene). The samples were subjected to 16 cycles of amplification under the following conditions: denaturation at 94° C. for 30 s, primer annealing at 55° C. for 1 min, and primer extension at 68° C. for 12 min 30 sec. Following PCR cycling, the PCR-product was digested with 10 U of DpnI to remove the methylated plasmid DNA template. E. coli XL1-Blue cells were transformed by heat shock with 4 μl of the PCR-Dpn I digested reaction containing the mutated plasmids and plated on an LB agar plate containing ampicillin. Colonies were randomly picked and cultivated overnight. Plasmid DNA was prepared using a QIAprep spin miniprep kit (Qiagen). The presence of desired mutations from cysteine to serine (C54S) was verified by nucleotide sequencing and the resulting plasmid was named pTB-shuttle-E-C54S. The sequence of the mutated ORF2b is given in SEQ ID NO: 7 ATGGGGTCT ATACAAAGCCTCTTCGACAAAATTG-GCCAGCTTTTTGTGGATGCTTTCACGGAATTTT TGGTGTCCATTGTTGATATCAT-CATATTTTTGGCCATTTTGTTTGGCTTCACCATCGCC GGTTGGCTGGTGGTCTTTTGCATCAGAT-TGGTTAGCTCCGCGGTATTCCGTGCGCGCC CTGC-CATTCACCCTGAGCAATTACAGAAGATCCTATGA, and the encoded peptide is given in SEQ ID NO: 8 MGSIQS-LFDKIGQLFVDAFTEFLVSIVDII-IFLAILFGFTIAGWLVVF CIRLVSSAVFRARPAIH-PEQLQKIL.

Shuttle plasmid pTB-shuttle-E-C54S and the wild type full-length genomic clone pCMV-S-P129 both contain unique Eco47 III and BsrG I sites (positions 285 and 1,192, and positions 11,785 and 12,692, respectively). Each plasmid was digested with Eco47 III and BsrG I. The 908 bp Eco47 III-BsrG I fragment was gel-purified from pTB-shuttle-E-C54S, and the 17,984 bp Eco47 III-BsrG I fragment was gel-purified from pCMV-S-P129. The two fragments were ligated using T4 DNA ligase (Invitrogen) to construct a C54S-modified full-length genomic cDNA clone. *E. coli* strain DH5-a was transformed with 10 µl of the ligation reaction. Bacterial colonies were selected from LB plates containing ampicillin and plasmid DNAs were prepared. Based on Xma I digestion patterns, full-length clones were selected. The selected clones were sequenced to confirm the presence of C54S modification in the full-length genomic cDNA clone. The resulting plasmid was designated pCMV-S-P129-E-C54S.

MARC-145 cells were grown in Dulbecco's modified Eagle medium (DMEM) supplemented with 8% fetal bovine serum (FBS; Gibco BRL), penicillin (100 U/mil), and streptomycin (50 µg/ml) at 37° C. with 5% $CO_2$, Cells were seeded in 35 mm-diameter dishes and grown to 70% confluency. The cells were transfected for 24 h with 2 µg of pCMV-S-P129-E-C54S or parental pCMV-S-P129 plasmid DNA using Lipofectin (Invitrogen). The transfected cells were incubated at 37° C. in DMEM supplemented with 8% FBS for 5 days. PRRSV-specific cytopathic effect (CPE) was observed from 3 days post-transfection and further spread to neighboring cells was seen by 5 days post-transfection. The specificity of CPE was confirmed by immunofluorescence cell staining using a rabbit antiserum for nonstructural proteins nsp2 and nsp3, and the N-specific MAb SDOW17. The culture supernatants from transfected cells were harvested at 5 days post-transfection and designated 'P129-E-C54S passage 1' (P1). The passage-1 virus was used to inoculate fresh MARC-145 cells and the 5-day harvest was designated 'passage-2' (P2). The 'passage-3' virus was prepared in the same way as P2. Each viral passage was stored in 1 ml aliquots at −80° C. until use. Each passage of P129-E-C54S virus was titrated by plaque assay, and the titers were determined to be $1.5 \times 10^4$, $5 \times 10^5$, and $1 \times 10^4$ pfu/ml for passages 1, 2, and 3, respectively. Wild type P129 virus was generated from pCMV-S-P129 and titrated in parallel, yielding titers of $1 \times 10^3$, $1 \times 10^4$, and $5 \times 10^5$ pfu/ml for passages 1, 2, and 3 respectively.

Figure 2:
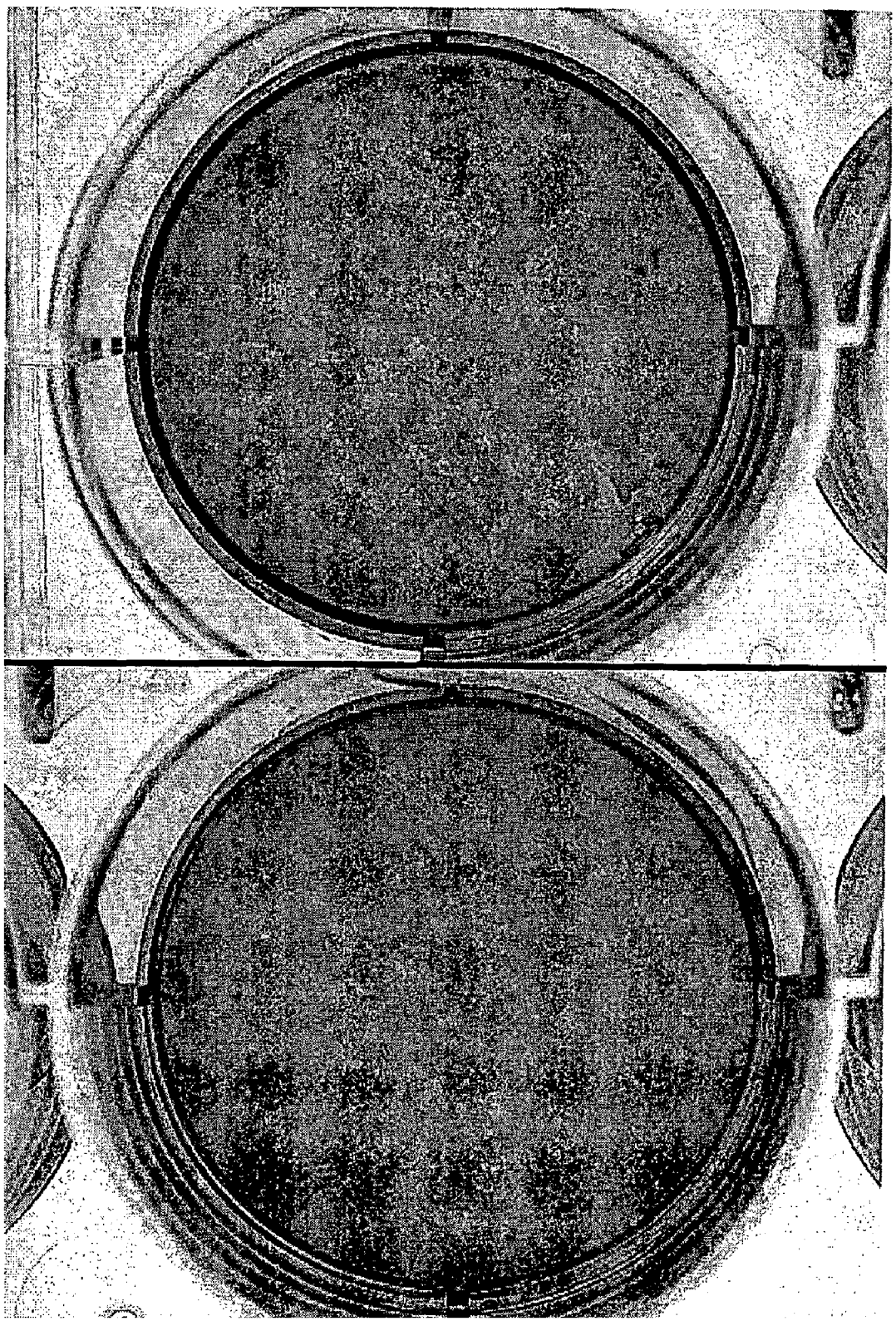
FIG. 2. Plaque morphology of parental P129 virus (top) and mutant P129-E-C54S virus (bottom). Monolayers of MARC-145 cells were infected, covered with an agarose overlay, incubated until plaques were apparent, and stained with neutral red to visualize the plaques. The mutant virus plaques are smaller, with more complete CPE in the centers.

The P129-E-C54S virus induced a distinct development of cytopathic effect (CPE) showing slow onset of CPE appearance and displayed a small-plaque phenotype relative to the P129 parental virus. Transfection of MARC-145 cells with either parental cDNA clone PCMV-S-P129 or mutant cDNA clone pCMV-S-P129-E-C54S resulted in visible foci of infected cells, and CPE mediated by the P129-E-C54S virus were very similar in size, but slower in appearance to that of the P129 parental virus by about day 4 post-transfection. However, the mutant virus caused rapid and extensive CPE thereafter (by about 5 days post-transfection) with areas of dead or detached cells within the foci, whereas the parental virus simply showed a modest increase in the size of the foci during the same time period. The difference in CPE is illustrated in FIG. 1. Viral titers corresponded with this difference in CPE, with the mutant yielding more progeny virus than the parent during the first two virus passages (but less in the third). The difference in plaque morphology is shown in FIG. 2. The P129-E-C54S virus produces plaques that are smaller in diameter and different in morphology, relative to parental P129 plaques. The P129-E-C454S plaques were more clear, due to cells in the center of the plaque dying and detaching sooner and more completely than in P129 plaques. Although there can be a number of biological explanations for a small-plaque phenotype, the observation of small plaques is direct evidence that the P129-E-C54S virus is spreading from cell to cell more slowly than its parent. This characteristic can be used in the current invention to generate an attenuated (less virulent) live vaccine virus from a virulent parent virus.

Indeed there are numerous examples of viruses that produce small plaque phenotypes and which are themselves attenuated in their natural hosts (Mathew et al., The extracellular domain of vaccinia virus protein B5R affects plaque phenotype, extracellular enveloped virus release, and intracellular actin tail formation. Journal of Virology. 72(3):2429-38, (1998); Engelstad et al., The vaccinia virus 42-kDa envelope protein is required for the envelopment and egress of extracellular virus and for virus virulence. Virology. 194(2): 627-37, (1993); Lewis et al., An African swine fever virus ERV1-ALR homologue, 9GL, affects virion maturation and viral growth in macrophages and viral virulence in swine. Journal of Virology. 74(3): 1275-85, (2000); Lee et al., Common E protein determinants for attenuation of glycosaminoglycan-binding variants of Japanese encephalitis and West Nile viruses. Journal of Virology. 78(15):8271-80 (2004); Frampton et al., Contribution of gene products encoded within the unique short segment of equine herpesvirus 1 to virulence in a murine model. Virus Research. 90(1-2):287-301, (2002); Lee, et al., Mechanism of virulence attenuation of glycosaminoglycan-binding variants of Japanese encephalitis virus and Murray Valley encephalitis virus. Journal of Virology. 76(10):4901-11, (2002); Butrapet et al., Attenuation markers of a candidate attenuated dengue type 2 vaccine virus, strain 16681 (PDK-53), are defined by mutations in the 5' noncoding region and nonstructural proteins 1 and 3. Journal of Virology. 74(7):3011-9, (2000)) The following example, derived from US Patent Publication 2002/0012670, provides clear guidance for the comparison of the virulent character of two different strains of PRRS viruses.

Example 3

Reversion-Resistant Mutations of Cysteine Residue 54

The C54S mutation described in example 2 is created by changing a single nucleotide in a single codon, from TGC (cysteine) to AGC (serine). Although adequate for determining the phenotype of the mutation, one would predict that the resulting virus might revert to the parental sequence (and parental phenotype) at a relatively high frequency due to random mutation and natural selection. Preferred embodiments of the invention, especially for vaccine purposes, would contain multiple nucleotide substitutions and/or deletions, designed to minimize the probability of the residue at position 54 reverting to cysteine, and to minimize the probability of other flanking residues (especially residues 51-57) mutating to become cysteines. Examination of the genetic code reveals that cysteine is encoded by only two codons (TGT and TGC). Use of codons that require two or three separate nucleotide mutation events to become cysteine codons are preferred over those that require only one. Examples of such "reversion resistant" mutations are shown in Table F, and are intended to be representative rather than limiting. Many other examples of reversion resistant mutations may be envisioned by one of ordinary skill in the art.

Mutation C54S-2 (see Table F) results in the same amino acid change as the C54S mutation, but the choice of serine codon is changed from AGC to TCG. Thus, two independent nucleotide mutations are required to generate a cysteine codon and the probability of phenotypic reversion is reduced relative to C54S. Mutation C54S-3 incorporates the same serine codon at position 54, but also alters the codons for leucine 52 (from TTG to CTG), valine 53 (from GTT to GTA), and serine 55 (from TCC to TCG). As a result, these three codons are less likely to mutate to cysteine codons and therefore less likely to functionally complement the absence of a cysteine residue at position 54. In the CS54-5SAA mutation, C54 and S55 are both mutated to encode alanine residues. Like serine, alanine possesses a small, uncharged side chain but lacks cysteine's capacity to form disulfide bonds or to interact with metal ions. Two of the four possible alanine codons (GCG and GCA) are sufficiently different from cysteine codons that all three nucleotide must be mutated in order to generate a cysteine codon. Therefore alanine substitutions are a preferred way to further reduce the possibility of phenotypic reversion. Finally, in the CS54-55delA mutation, the codon for position 54 is deleted. In addition, serine 55 is changed to alanine and the codons for leucine 52 and valine 53 are altered. Phenotypic reversion of such mutant viruses is predicted to be exceedingly rare.

When designing reversion resistant mutations, alternative codons can sometimes be selected in such a way that restriction enzyme recognition sites are created or destroyed. These differences can serve as convenient markers for distinguishing mutated from non-mutated plasmids and viruses. In the case of mutations C54S-3, CS54-55AA, and CS54-55delA (Table F), mutation of the S55 codon TCC to either TCG (serine) or GCG (alanine) results in the destruction of a naturally occurring SacII restriction site (CCGCGG).

Since ORF2b overlaps ORF2a (which encodes GP2 in a different reading frame), one must be cautious not to introduce termination codons into ORF2a in the process of modifying codons in ORF2b. In some cases, codon changes to ORF2b can alter the amino acid sequence encoded by ORF2a. The effect of such changes on GP2 protein function can be difficult to predict and are best determined empirically.

Example 4

Establishment of Attenuation

At least 10 gilts per group are included in each trial, which are derived from a PRRSV-free farm.

Animals are tested free of PRRS virus specific serum antibodies and negative for PRRSV. All animals included in the trial are of the same source and breed. The allocation of the animals to the groups is randomized.

Challenge is performed at day 90 of pregnancy with intranasal application of 1 ml PRRSV with $10^5$ TCID$_{50}$ per nostril. There are at least three groups for each test setup: One group for P129 challenge; one test group for challenge with the possibly attenuated virus; and one strict control group.

The study is deemed valid when the strict controls stay PRRSV-negative over the time course of the study and at least 25% less live healthy piglets are born in the P129 challenged group compared to the strict controls.

Attenuation, in other words less virulence, is defined as the statistical significant change of one or more parameters determining reproductive performance:

Significant reduction in at least one of the following parameters for the test group (possibly attenuated virus) compared to the P129 infected group is preferred:

a.) frequency of stillborns b.) abortion at or before day 112 of pregnancy

TABLE F

| Designation | Nucleotide Sequence (genome positions 12,212-12,232 shown). Mutated nucleotides are underlined. | Amino Acid sequence (E protein residues 51-57). Mutated residues are underlined. | Forward (F) and Reverse (R) Mutagenic Primers (genome positions 12,207-12,238 for the first two primer pairs, genome positions 12,203-12,242 for the remaining primer pairs). Mutated nucleotides are underlined. |
|---|---|---|---|
| WT ("wild-type", parental) | SEQ ID NO: 9<br>AGATTGGTTTGCTCCGCGGTA | SEQ ID NO: 10<br>RLVCSAV | Not Applicable |
| C54S | SEQ ID NO: 11<br>AGATTGGTTAGCTCCGCGGTA | SEQ ID NO: 12<br>RLVSSAV | SEQ ID NO: 13<br>F-GCATGAGATTGGTTAGCTCCGCGGTATTCCG<br>SEQ ID NO: 14<br>R-CGGAATACCGCGGAGCTAACCAATCTCATGC |
| C54S-2 | SEQ ID NO: 15<br>AGATTGGTTTCGTCCGCGGTA | SEQ ID NO: 16<br>RLVSSAV | SEQ ID NO: 17<br>F-GCATGAGATTGGTTTCGTCCGCGGTATTCCG<br>SEQ ID NO: 18<br>R-CGGAATACCGCGGACGAAACCAATCTCATGC |
| C54S-3 | SEQ ID NO: 19<br>AGACTGGTATCGTCGGCGGTA | SEQ ID NO: 20<br>RLVSSAV | SEQ ID NO: 21<br>F-TTTTGCATGAGACTGGTATCGTCGGCGGTATTCCGTGCG<br>SEQ ID NO: 22<br>R-CGCACGGAATACCGCCGACGATACCAGTCTCATGCAAAA |
| CS54-55AA | SEQ ID NO: 23<br>AGACTGGTGGCGGCGGCGGTA | SEQ ID NO: 24<br>RLVAAAV | SEQ ID NO: 25<br>F-TTTTGCATGAGACTGGTGGCGGCGGCGGTATTCCGTGCG<br>SEQ ID NO: 26<br>R-CGCACGGAATACCGCCGCCGCCACCAGTCTCATGCAAAA |
| CS54-55delA | SEQ ID NO: 27<br>AGACTGGTG---GCGGCGGTA | SEQ ID NO: 28<br>RLV-AAV | SEQ ID NO: 29<br>F-TTTTGCATGAGACTGGTGGCGGCGGTATTCCGTGCG<br>SEQ ID NO: 30<br>R-CGCACGGAATACCGCCGCCACCAGTCTCATGCAAAA | c.) number of mummified piglets d.) number of less lively and weak piglets e.) preweaning mortality Furthermore a significant increase in one of the following parameters for the test group compared to the P129-infected group is preferred:

f.) number of piglets weaned per sow g.) number of live healthy piglets born per sow Vaccines An attenuated strain is valuable for the formulation of vaccines. The present vaccine is effective if it protects a pig against infection by a PRRS virus. A vaccine protects a pig against infection by a PRRS virus if, after administration of the vaccine to one or more unaffected pigs, a subsequent challenge with a biologically pure virus isolate (e.g., VR 2385, VR 2386, P129 etc.) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 4 weeks), challenging with a large sample ($10^{(3-7)}TCID_{(50)}$) of a biologically pure PRRSV isolate. A blood sample is then drawn from the challenged pig after about one week, and an attempt to isolate the virus from the blood sample is then performed (e.g., see the virus isolation procedure exemplified in Experiment VIII below). Isolation of high levels of the virus (similar to unvaccinated, challenged control pigs) is an indication that the vaccine may not be effective. Failure to isolate the virus, or isolation of a reduced amount of virus, is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil, or lymph node tissue sample by an immunoassay method). The symptoms of the porcine reproductive and respiratory disease may be evaluated quantitatively (e.g., temperature/fever), semi-quantitatively (e.g., severity of respiratory distress [explained in detail below], or qualitatively (e.g., the presence or absence of one or more symptoms or a reduction in severity of one or more symptoms, such as cyanosis, pneumonia, heart and/or brain lesions, etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one that shows symptoms of PRRS or from which PRRSV can be isolated.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM ½ formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 pg/ml Quil A, 100 [mgr]g/ml cholesterol, and 0.5% (v/v) lecithin. Modified SEAM ½ is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: Drugs and the Pharmaceutical Sciences, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably-chosen-after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about 10 to about $10^7$ pfu. The dose amount of a plasmid of the present invention in a vaccine of the present invention preferably ranges from about 0.1 µg to about 100 mg, more preferably from about 1 µg to about 10 mg, even more preferably from about 10 µg to about 1 mg. The dose amount of an infectious RNA molecule of the present invention in a vaccine of the present invention preferably ranges from about 0.1 to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

The present invention further provides a method of preparing a vaccine comprising a PRRS virus, infectious RNA molecule, plasmid, or viral vector described herein, which method comprises combining an effective amount of one of the PRRS virus, infectious RNA molecule, plasmid, or viral vector of the present invention, with a carrier acceptable for pharmaceutical or veterinary use.

In addition the live attenuated vaccine of the present invention can be modified as described in U.S. Pat. No. 6,500,662 to encode a heterologous antigenic epitope which is inserted into the PRRS viral genome using known recombinant techniques. Antigenic epitopes useful as heterologous antigenic epitopes for the present invention include antigenic epitopes from a swine pathogen other than PRRS virus which include, but are not limited to, an antigenic epitope from a swine pathogen selected from the group consisting of porcine parvovirus, porcine circovirus, a porcine rotavirus, swine influenza, pseudorabies virus, transmissible gastroenteritis virus, porcine respiratory coronavirus, classical swine fever virus, African swine fever virus, encephalomyocarditis virus, porcine paramyxovirus, *Actinobacillus pleuropneumoni*, *Bacillus anthraci*, *Bordetella bronchiseptica*, *Clostridium haemolyticum*, *Clostridium perfringens*, *Clostridium tetani*, *Escherichia coli*, *Erysipelothdix rhusiopathiae*, *Haemophilus parasuis*, *Leptospira* spp., *Mycoplasma hyopneumoniae*, *Mycoplasma hyorhinis*, *Pasteurella haemolytica*, *Pasteurella multocida*, *Salmonella choleraesuis*, *Salmonella typhimurium*, *Streptococcus equismilis*, and *Streptococcus suis*. Nucleotide sequences encoding antigenic epitopes from the aforementioned swine pathogens are known in the art and can be obtained from public gene databases such as GenBank (http://www.ncbi.nlm.nih.gov/Web/Genbank/index.html) provided by NCBI.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations that are described herein as critical to the invention should be viewed as such; variations of the invention which have not been described herein as critically limiting are intended as aspects of the invention. It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference.

SEQUENCE LISTING

```
<160> NUMBER OF SEQ ID NOS: 32

<210> SEQ ID NO 1
<211> LENGTH: 27
<212> TYPE: DNA
<213> ORGANISM: Porcine reproductive and respiratory syndrome virus

<400> SEQUENCE: 1
actcagtcta agtgctggaa agttatg                                            27

<210> SEQ ID NO 2
<211> LENGTH: 27
```

<212> TYPE: DNA
<213> ORGANISM: Porcine reproductive and respiratory syndrome virus

<400> SEQUENCE: 2
atcttatcat gtctggatcc ccgcggc                                              27

<210> SEQ ID NO 3
<211> LENGTH: 31
<212> TYPE: DNA
<213> ORGANISM: Porcine reproductive and respiratory syndrome virus

<400> SEQUENCE: 3
gcatcagatt ggttagctcc gcggtattcc g                                         31

<210> SEQ ID NO 4
<211> LENGTH: 31
<212> TYPE: DNA
<213> ORGANISM: Porcine reproductive and respiratory syndrome virus

<400> SEQUENCE: 4
cggaataccg cggagctaac caatctgatg c                                         31

<210> SEQ ID NO 5
<211> LENGTH: 73
<212> TYPE: PRT
<213> ORGANISM: Porcine reproductive and respiratory syndrome virus

<400> SEQUENCE: 5

Met Gly Ser Ile Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
            20                  25                  30

Leu Ala Ile Leu Phe Gly Phe Thr Ile Ala Gly Trp Leu Val Val Phe
        35                  40                  45

Cys Ile Arg Leu Val Cys Ser Ala Val Phe Arg Ala Arg Pro Ala Ile
    50                  55                  60

His Pro Glu Gln Leu Gln Lys Ile Leu
65                  70

<210> SEQ ID NO 6
<211> LENGTH: 222
<212> TYPE: DNA
<213> ORGANISM: Porcine reproductive and respiratory syndrome virus

<400> SEQUENCE: 6
atggggtcta tacaaagcct cttcgacaaa attggccagc tttttgtgga tgctttcacg         60
gaattttggg tgtccattgt tgatatcatc atattttttgg ccattttgtt tggcttcacc        120
atcgccggtt ggctggtggt cttttgcatc agattggttt gctccgcggt attccgtgcg        180
cgccctgcca ttcaccctga gcaattacag aagatcctat ga                            222

<210> SEQ ID NO 7
<211> LENGTH: 222
<212> TYPE: DNA
<213> ORGANISM: Porcine reproductive and respiratory syndrome virus

<400> SEQUENCE: 7
atggggtcta tacaaagcct cttcgacaaa attggccagc tttttgtgga tgctttcacg         60
gaattttggg tgtccattgt tgatatcatc atattttttgg ccattttgtt tggcttcacc        120
atcgccggtt ggctggtggt cttttgcatc agattggtta gctccgcggt attccgtgcg        180

-continued cgccctgcca ttcaccctga gcaattacag aagatcctat ga        222

<210> SEQ ID NO 8
<211> LENGTH: 73
<212> TYPE: PRT
<213> ORGANISM: Porcine reproductive and respiratory syndrome virus

<400> SEQUENCE: 8

Met Gly Ser Ile Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
                20                  25                  30

Leu Ala Ile Leu Phe Gly Phe Thr Ile Ala Gly Trp Leu Val Val Phe
            35                  40                  45

Cys Ile Arg Leu Val Ser Ser Ala Val Phe Arg Ala Arg Pro Ala Ile
        50                  55                  60

His Pro Glu Gln Leu Gln Lys Ile Leu
65                  70

<210> SEQ ID NO 9
<211> LENGTH: 21
<212> TYPE: DNA
<213> ORGANISM: Porcine reproductive and respiratory syndrome virus

<400> SEQUENCE: 9
agattggttt gctccgcggt a        21

<210> SEQ ID NO 10
<211> LENGTH: 7
<212> TYPE: PRT
<213> ORGANISM: Porcine reproductive and respiratory syndrome virus

<400> SEQUENCE: 10

Arg Leu Val Cys Ser Ala Val
1               5

<210> SEQ ID NO 11
<211> LENGTH: 21
<212> TYPE: DNA
<213> ORGANISM: Porcine reproductive and respiratory syndrome virus

<400> SEQUENCE: 11
agattggtta gctccgcggt a        21

<210> SEQ ID NO 12
<211> LENGTH: 7
<212> TYPE: PRT
<213> ORGANISM: Porcine reproductive and respiratory syndrome virus

<400> SEQUENCE: 12

Arg Leu Val Ser Ser Ala Val
1               5

<210> SEQ ID NO 13
<211> LENGTH: 31
<212> TYPE: DNA
<213> ORGANISM: Porcine reproductive and respiratory syndrome virus

<400> SEQUENCE: 13
gcatgagatt ggttagctcc gcggtattcc g        31

```
<210> SEQ ID NO 14
<211> LENGTH: 31
<212> TYPE: DNA
<213> ORGANISM: Porcine reproductive and respiratory syndrome virus

<400> SEQUENCE: 14
cggaataccg cggagctaac caatctcatg c                                31

<210> SEQ ID NO 15
<211> LENGTH: 21
<212> TYPE: DNA
<213> ORGANISM: Porcine reproductive and respiratory syndrome virus

<400> SEQUENCE: 15
agattggttt cgtccgcggt a                                           21

<210> SEQ ID NO 16
<211> LENGTH: 7
<212> TYPE: PRT
<213> ORGANISM: Porcine reproductive and respiratory syndrome virus

<400> SEQUENCE: 16

Arg Leu Val Ser Ser Ala Val
1               5

<210> SEQ ID NO 17
<211> LENGTH: 31
<212> TYPE: DNA
<213> ORGANISM: Porcine reproductive and respiratory syndrome virus

<400> SEQUENCE: 17
gcatgagatt ggtttcgtcc gcggtattcc g                                31

<210> SEQ ID NO 18
<211> LENGTH: 31
<212> TYPE: DNA
<213> ORGANISM: Porcine reproductive and respiratory syndrome virus

<400> SEQUENCE: 18
cggaataccg cggacgaaac caatctcatg c                                31

<210> SEQ ID NO 19
<211> LENGTH: 21
<212> TYPE: DNA
<213> ORGANISM: Porcine reproductive and respiratory syndrome virus

<400> SEQUENCE: 19
agactagtat cgtcggcggt a                                           21

<210> SEQ ID NO 20
<211> LENGTH: 7
<212> TYPE: PRT
<213> ORGANISM: Porcine reproductive and respiratory syndrome virus

<400> SEQUENCE: 20

Arg Leu Val Ser Ser Ala Val
1               5

<210> SEQ ID NO 21
<211> LENGTH: 39
<212> TYPE: DNA
<213> ORGANISM: Porcine reproductive and respiratory syndrome virus

<400> SEQUENCE: 21
```

-continued

```
ttttgcatga gactagtatc gtcggcggta ttccgtgcg                                39
```

<210> SEQ ID NO 22
<211> LENGTH: 39
<212> TYPE: DNA
<213> ORGANISM: Porcine reproductive and respiratory syndrome virus

<400> SEQUENCE: 22

```
cgcacggaat accgccgacg atactagtct catgcaaaa                                39
```

<210> SEQ ID NO 23
<211> LENGTH: 21
<212> TYPE: DNA
<213> ORGANISM: Porcine reproductive and respiratory syndrome virus

<400> SEQUENCE: 23

```
agactagtag cggcggcggt a                                                   21
```

<210> SEQ ID NO 24
<211> LENGTH: 7
<212> TYPE: PRT
<213> ORGANISM: Porcine reproductive and respiratory syndrome virus

<400> SEQUENCE: 24

Arg Leu Val Ala Ala Ala Val
1               5

<210> SEQ ID NO 25
<211> LENGTH: 39
<212> TYPE: DNA
<213> ORGANISM: Porcine reproductive and respiratory syndrome virus

<400> SEQUENCE: 25

```
ttttgcatga gactagtagc ggcggcggta ttccgtgcg                                39
```

<210> SEQ ID NO 26
<211> LENGTH: 39
<212> TYPE: DNA
<213> ORGANISM: Porcine reproductive and respiratory syndrome virus

<400> SEQUENCE: 26

```
cgcacggaat accgccgccg ctactagtct catgcaaaa                                39
```

<210> SEQ ID NO 27
<211> LENGTH: 18
<212> TYPE: DNA
<213> ORGANISM: Porcine reproductive and respiratory syndrome virus

<400> SEQUENCE: 27

```
agactggtgg cggcggta                                                       18
```

<210> SEQ ID NO 28
<211> LENGTH: 6
<212> TYPE: PRT
<213> ORGANISM: Porcine reproductive and respiratory syndrome virus

<400> SEQUENCE: 28

Arg Leu Val Ala Ala Val
1               5

```
<210> SEQ ID NO 29
<211> LENGTH: 36
<212> TYPE: DNA
<213> ORGANISM: Porcine reproductive and respiratory syndrome virus

<400> SEQUENCE: 29
ttttgcatga gactagtagc ggcggtattc cgtgcg                              36

<210> SEQ ID NO 30
<211> LENGTH: 36
<212> TYPE: DNA
<213> ORGANISM: Porcine reproductive and respiratory syndrome virus

<400> SEQUENCE: 30
cgcacggaat accgccgcta ctagtctcat gcaaaa                              36

<210> SEQ ID NO 31
<211> LENGTH: 73
<212> TYPE: PRT
<213> ORGANISM: Porcine reproductive and respiratory syndrome virus

<400> SEQUENCE: 31

Met Gly Ser Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
                20                  25                  30

Leu Ala Ile Leu Phe Gly Phe Thr Ile Ala Gly Trp Leu Val Val Phe
            35                  40                  45

Cys Ile Arg Leu Val Cys Ser Ala Ile Leu Arg Thr Arg Pro Ala Ile
        50                  55                  60

His Ser Glu Gln Leu Gln Lys Ile Leu
65                  70

<210> SEQ ID NO 32
<211> LENGTH: 70
<212> TYPE: PRT
<213> ORGANISM: Porcine reproductive and respiratory syndrome virus

<400> SEQUENCE: 32

Met Gly Ser Leu Trp Ser Lys Ile Ser Gln Leu Phe Val Asp Ala Phe
1               5                   10                  15

Thr Glu Phe Leu Val Ser Val Val Asp Ile Ala Ile Phe Leu Ala Ile
                20                  25                  30

Leu Phe Gly Phe Thr Val Ala Gly Trp Leu Leu Val Phe Leu Leu Arg
            35                  40                  45

Val Val Cys Ser Ala Leu Leu Arg Ser Arg Ser Ala Ile His Ser Pro
        50                  55                  60

Glu Leu Ser Lys Val Leu
65                  70
```

What is claimed is:

1. An isolated polynucleotide that comprises:
   (a) a DNA molecule or its complement, that encodes a genetically modified PRRS virus, wherein the encoding sequence of the E protein thereof has been mutated, such that the conserved cysteine residue that corresponds to residue 54 in North American genotype viruses and residue 51 in European genotype viruses, is either deleted, or replaced with a non-cysteine residue, wherein the virus is attenuated as a result of said modification, and with the proviso that the non-cysteine residue is not tyrosine; or;
   (b) an infectious RNA molecule encoding the genetically modified PRRS virus of (a).

2. The isolated polynucleotide of claim 1, wherein the original codon corresponding to said conserved cysteine residue of said E protein has been deleted, or mutated to provide a resultant codon for serine or alanine, said polynucleotide optionally further comprising an additional codon mutation within two codons of the codon for the conserved cysteine to minimize (1) the probability of reversion of said resultant codon back to a cysteine codon, or (2) the mutation of a codon adjacent to said original cysteine codon to a further cysteine codon.

3. The polynucleotide according to claim 2 wherein:
   (a) said serine codon differs by at least 2 nucleotides from any cysteine codon; or
   (b) said alanine codon differs by 3 nucleotides from any cysteine codon; or
   (c) an adjacent codon, that is one or two codons upstream or downstream from said conserved cysteine codon, is mutated such that said adjacent codon still encodes the same amino acid, but at least two nucleotides thereof would need to be changed to before said adjacent codon would encode cysteine; or
   (d) an adjacent codon, that is one or two codons upstream or downstream from said conserved cysteine codon, is mutated such that said adjacent codon encodes a different amino acid, and at least two nucleotides thereof would need to be changed before said adjacent codon would encode cysteine.

4. The polynucleotide of claim 1 wherein the codon for the conserved cysteine has been replaced by a codon for serine, threonine, or methionine.

5. A genetically modified PRRS virus encoded by any of the polynucleotides of claim 1.

6. A genetically modified PRRS virus encoded by any of the polynucleotides of claims 2.

7. A genetically modified PRRS virus encoded by any of the polynucleotides of claim 3.

8. A genetically modified PRRS virus encoded by any of the polynucleotides of claim 4.

9. The virus of claim 5 wherein the modification results in a small plaque phenotype virus.

10. A method of inducing an immune response against PRRS virus in a porcine animal, which comprises administering an effective immunizing amount of the virus of claim 5.

11. An immunogenic composition that comprises the polynucleotide of claim 1, and a carrier acceptable for veterinary use.

12. An immunogenic composition that comprises the genetically modified PRRS virus of claim 5, and a carrier acceptable for veterinary use.

13. A method for making a genetically modified North American PRRS virus, which method comprises: a) mutating a DNA sequence encoding an infectious RNA molecule which encodes a PRRS virus, to produce a genetically modified PRRS virus wherein the conserved cysteine in the E protein that corresponds to residue 54 in North American genotype viruses and residue 51 in European genotype viruses has been changed to a non-cysteine residue; and b) introducing the genetically modified North American PRRS virus into a host cell capable of supporting PRRS virus replication.

14. The method of claim 13 wherein the host cell capable of supporting PRRS replication is a MARC-145 cell.

15. The method of claim 13 wherein the host cell capable of supporting PRRS replication is comprised within a live porcine animal.

16. An isolated host cell transfected with the polynucleotide of claim 1.

17. An isolated host cell infected with the virus of claim 5.

* * * * *